United States Patent [19]

Li

[11] Patent Number: 4,547,484

[45] Date of Patent: * Oct. 15, 1985

[54] METHOD OF PREPARING A CATALYST FOR THE OXIDATION AND AMMOXIDATION OF OLEFINS

[75] Inventor: Tao P. Li, Chesterfield, Mo.

[73] Assignee: Monsanto Company, St. Louis, Mo.

[*] Notice: The portion of the term of this patent subsequent to Dec. 11, 2001 has been disclaimed.

[21] Appl. No.: 654,428

[22] Filed: Sep. 26, 1984

Related U.S. Application Data

[63] Continuation-in-part of Ser. No. 598,130, Apr. 9, 1984, Pat. No. 4,487,850, which is a continuation-in-part of Ser. No. 568,774, Jan. 6, 1984, abandoned, which is a continuation-in-part of Ser. No. 430,053, Sep. 30, 1982, abandoned.

[51] Int. Cl.$^4$ .......................... B01J 23/84; B01J 23/88
[52] U.S. Cl. ...................................... 502/249; 502/311
[58] Field of Search ................................ 502/249, 311

[56] References Cited

U.S. PATENT DOCUMENTS 4,018,712  4/1977  Li .................................... 502/249

*Primary Examiner*—W. J. Shine
*Attorney, Agent, or Firm*—Thomas N. Wallin

[57] ABSTRACT

A method for the preparation of catalysts useful for the oxidation and ammoxidation of olefins contain antimony, uranium, iron, bismuth, and molybdenum in a catalytically active oxidized state. The method comprises preparing a hydrated mixed oxide component containing antimony, uranium iron and bismuth, making an aqueous slurry thereof; adding a molybdate thereto; adjusting the pH, drying and calcining. The catalysts are especially useful for the production of acrylonitrile from propylene, ammonia, and an oxygen-containing gas.

14 Claims, No Drawings

METHOD OF PREPARING A CATALYST FOR THE OXIDATION AND AMMOXIDATION OF OLEFINS

BACKGROUND OF THE INVENTION

This application is a continuation in part of my copending patent application Ser. No. 598,130 filed, Apr. 9, 1984, now U.S. Pat. No. 4,487,850 which was a continuation-in-part of my copending patent application, Ser. No. 568,774 (now abandoned), filed Jan. 6, 1984, which was a continuation in part of application, Ser. No. 430,053 (now abandoned), filed Sept. 30, 1982.

FIELD OF THE INVENTION

This invention relates to oxidation and/or ammoxidation catalysts containing the elements iron, antimony, uranium, iron, bismuth, and molybdenum in a catalytically active oxidized state and to a process for preparing such catalysts. It is well known that olefins can be oxidized to oxygenated hydrocarbons such as unsaturated aldehydes and acids, for example, acrolein and methacrolein, and acrylic acid and methacrylic acid.

It is also well known that olefins can be ammoxidized to unsaturated nitriles such as acrylonitrile and methacrylonitrile. The value of such oxygenated hydrocarbons and unsaturated nitriles is generally well recognized, with acrylonitrile being among the most valuable monomers available to the polymer industry for producing useful polymeric products.

DESCRIPTION OF THE PRIOR ART

Various catalytic processes are known for the oxidation and/or ammoxidation of olefins. Such processes commonly react an olefin or an olefin-ammonia mixture with oxygen in the vapor phase in the presence of a catalyst. For the production of acrolein and acrylonitrile, propylene is the generally used olefin reactant, and for the production of methacrolein and methacrylonitrile, isobutylene is the generally used olefin reactant.

Many catalysts are disclosed as suitable in the oxidation and ammoxidation of olefins. One such catalyst is described in U.S. Pat. No. 4,018,712. This catalyst is represented by the empirical formula:

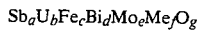

wherein Me is nickel or cobalt, a is 1 to 10, b is 0.1 to 5, c is 0.1 to 5, d is 0.001 to 0.1, e is 0.001 to 0.1, f is 0 to 0.1, and g is a number taken to satisfy the valences of the quantities of Sb, U, Fe, Bi, and Mo, including Ni and Co if present, in the oxidation states in which they exist in the catalyst.

Although the yield and selectivity of the above-described catalysts are generally satisfactory, the commercial utility of a catalyst system is highly dependent upon the cost of the system, the conversion of the reactant(s), the yield of the desired product(s), and the stability of the catalyst during operation. In many cases, a reduction in the cost of a catalyst system on the order of a few cents per pound or a small percent increase in the yield of the desired product represents a tremendous commercial economical advantage. And since it is well known that the economics of acrylonitrile manufacture dictate increasingly higher yields and selectivity of conversion of reactants to acrylonitrile in order to minimize the difficulties attending the purification of the product and handling of large recycle streams, research efforts are continually being made to define new or improved catalyst systems and methods and processes of making new and old catalyst systems to reduce the cost and/or upgrade the activity and selectivity of such catalyst systems. The discovery of the method of preparing the improved catalysts of the present invention is therefore believed to be a decided advance in the state of the art.

SUMMARY OF THE INVENTION

It is the object of this invention to provide a stabilized catalyst containing the elements antimony, uranium, iron, bismuth, and molybdenum in a catalytically active oxidized state useful in the preparation of unsaturated nitriles by ammoxidation of olefins, characterized by high activity and selectivity to the nitriles.

Another object of this invention is to provide a catalyst which is useful for the oxidation of olefins to the corresponding unsaturated aldehyde.

A further object of this invention is to provide an improved process for the preparation of a catalyst containing oxygen, antimony, uranium, iron, bismuth, and molybdenum.

Yet another object of this invention is to provide an ammoxidation process which employs such a catalyst.

To achieve these and other objects which will become apparent from the accompanying description and claims, a catalyst is provided which contains the elements antimony, uranium, iron, bismuth, and molybdenum in a catalytically active oxidized state represented by the empirical formula:

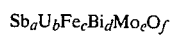

wherein a is 1 to 10, b is 0.1 to 5, c is 0.1 to 5, d is 0.001 to 0.1, e is 0.001 to 0.2, f is a number taken to satisfy the valence requirements of Sb, U, Fe, Bi, and Mo in the oxidation states in which they exist in the catalyst. According to the present invention, such a catalyst is prepared by (a) preparing a hydrated mixed oxides component containing antimony, uranium, iron, and bismuth by the steps of
 (i) forming a mixture of oxides or nitrates of bismuth and uranium and an oxide of antimony in nitric acid,
 (ii) heating the mixed oxides mixture at a temperature and for a time sufficient to induce formation of crystalline oxides of antimony,
 (iii) adding an aqueous solution of ferric nitrate to the mixed oxides mixture,
 (iv) adjusting the pH of the mixed oxides mixture to about 8, thereby forming a hydrated mixed oxide precipitate in an aqueous phase, and
 (v) separating the hydrated mixed oxides from the aqueous phase
(b) forming an aqueous slurry of the hydrated mixed oxides component;
(c) adjusting the pH of the hydrated mixed oxides component slurry to about 9;
(d) adding a molybdate to the hydrated mixed oxides component slurry;
(e) adjusting the pH of the hydrated mixed oxides component—molybdate component slurry to about 8–9;

(f) forming the hydrated mixed oxides component—molybdate component slurry into dry particles; and (g) calcining the dry particles to form the active catalyst.

DESCRIPTION OF THE PREFERRED EMBODIMENTS

In accordance with this invention, a catalyst containing antimony, uranium, iron, bismuth, and molybdenum in a catalytically active oxidized state useful for the oxidation and/or ammoxidation of olefins is represented by the empirical formula:

$$Sb_aU_bFe_cBi_dMo_eO_f$$

where a is 1 to 10, b is 0.1 to 5, c is 0.1 to 5, d is 0.001 to 0.1, e is 0.001 to 0.2, f is a number taken to satisfy the valence requirements of Sb, U, Fe, Bi, and Mo in the oxidation states in which they exist in the catalyst. The catalysts are prepared by an improved process which comprises:

(a) preparing a hydrated mixed oxides component containing antimony, uranium, iron, and bismuth by the steps of
  (i) forming a mixture of oxides or nitrates of bismuth and uranium and an oxide of antimony in nitric acid,
  (ii) heating the mixed oxides mixture at a temperature and for a time sufficient to induce formation of crystalline oxides of antimony,
  (iii) adding an aqueous solution of ferric nitrate to the mixed oxides mixture,
  (iv) adjusting the pH of the mixed oxides mixture to about 8, thereby forming a hydrated mixed oxide precipitate in an aqueous phase,
  (v) separating the hydrated mixed oxides from the mixed oxides mixture, and washing occluded impurities from the hydrated mixed oxides;

(b) forming an aqueous slurry of the hydrated mixed oxides component;

(c) adjusting the pH of the hydrated mixed oxides component slurry to about 9;

(d) adding a molybdate to the hydrated mixed oxides component slurry;

(e) adjusting the pH of the hydrated mixed oxides component—molybdate component slurry to about 8–9;

(f) forming the hydrated mixed oxides component—molybdate component slurry into dry particles; and (g) calcining the dry particles to form the active catalyst.

The catalyst of the present invention, is prepared under narrowly prescribed critical conditions. A hydrated mixed oxides component containing antimony, uranium, iron, and bismuth is intimately mixed with a ferric molybdate component (the preparation of each of these components being described below). The mixing of the components is accomplished in an aqueous slurry at a pH of about 9. Specifically, the hydrated mixed oxides component is first slurried in water at the prescribed pH. A catalyst support may be added, if desired, along with the hydrated mixed oxides component. In either case, whether a support is present or absent, a molybdate is then added to the slurry. The resultant slurry is ball milled for about 18 hours or until the solid particles are reduced to a size less than 10 microns in diameter. Thereafter, the pH of the slurry is adjusted, if necessary to about 8–9.

At this point, the intimately mixed slurry is heated to remove the bulk of the aqueous phase. The concentrated slurry contains a certain amount of water and it is desirable to remove this water by some form of drying process to form a dry catalyst precursor. This can take the form of a simple oven drying process in which the water-containing solid phase is subjected to a temperature that is sufficiently high to vaporize the water and completely dry the solid phase.

An alternate drying process which may be employed is the so-called spray-drying process. In this process, which is preferred for use in the present invention, water-containing solid phase particles are sprayed into contact with hot gas (usually air) so as to vaporize the water. The drying is controlled by the temperature of the gas and the distance the particles travel in contact with the gas. It is generally desirable to adjust these parameters to avoid too rapid drying as this results in a tendency to form dried skins on the partially dried particles of the solid phase which are subsequently ruptured as water occluded within the particles vaporizes and attempts to escape. At the same time, it is desirable to provide the catalyst in a form having as little occluded water as possible. Therefore, where a fluidized bed reactor is to be used and microspheroidal particles are desired, it is advisable to choose the conditions of spray-drying with a view to achieving substantial complete drying without particle rupture.

Following the drying operation, the catalyst precursor is calcined to form the active catalyst. The calcination is usually conducted in air at essentially atmospheric pressure and at a temperature of about 500° C. to about 1150° C., preferably from about 750° C. to about 900° C. The time to complete the calcination can vary and will depend upon the temperature employed. In general the time can be anything up to 24 hours, but for most purposes, a time period from about 1 hour to about 3 hours at the designated temperatures is sufficient.

The catalyst can be employed without a support and will display excellent activity. However, in some applications, it may be advantageous to include in the catalyst a support material which functions by providing a large surface area for the catalyst and by creating a harder and more durable catalyst for use in the highly abrasive environment of a fluidized bed reactor. This support material can be any of those commonly proposed for such use, such as, for example, silica, zirconia, alumina, titania, antimony pentoxide sol, or other oxide substrates. From the point of view of availability, cost, and performance, silica is usually a satisfactory support material and is preferably in the form of silica sol for easy dispersion.

The proportions in which the components of the supported catalysts are present can vary widely, but it is usually preferred that the support provides from about 10% to about 90% and more preferably about 35% to about 65% by weight of the total combined weight of the catalyst and the support. To incorporate a support into the catalyst, the support material is preferably slurried along with the hydrated mixed oxide component in water at a pH of 9 while maintaining slurry fluidity.

As previously noted, the hydrated mixed oxides component contains antimony, uranium, iron, and bismuth. It is prepared by mixing the oxides or nitrates of bismuth and uranium and an oxide of antimony (usually antimony trioxide) with nitric acid. A critical feature of the instant invention is the heating of the antimony trioxide in the nitric acid. By so doing, the initially amorphous antimony trioxide is converted to crystalline oxides of antimony. In addition, at least a portion of the antimony trioxide is converted to higher oxidation states such as antimony tetroxide and antimony pentoxide.

The time required to induce the formation of the desired crystalline oxides of antimony can vary and will depend, at least in part, on the temperature employed. Generally, a time period of about 2 hours to about 6 hours at temperatures from about 90° C. to about 110° C., preferably at least 100° C., is sufficient.

After the heating period is completed, an aqueous solution of ferric nitrate [$Fe(NO_3)_3 \cdot 9H_2O$] is added to the mixed oxides mixture, optionally having been cooled to ambient temperatures prior to the ferric nitrate addition. The pH of the resultant mixture is adjusted to about 8 using aqueous ammonia. The resulting hydrated mixed oxides precipitate is then separated from the aqueous phase and thoroughly washed with slightly alkaline water (pH 8) to remove substantially all occluded impurities, most notably ammonium nitrate.

The molybdate may be introduced as any compound which does not interfere with catalysis or neutralize the catalyst. Ferric molybdate and ammonium molybdate have been successfully employed to introduce the molybdate. Ammonium molybdate is preferred, being the simplest to prepare (from molybdenum trioxide and aqueous ammonia). Ferric molybdate may be prepared by combining stoichiometric amounts of aqueous solutions of ammonium molybdate (prepared by dissolving molybdenum trioxide in aqueous ammonia) and ferric nitrate. Since the ammonium molybdate is essentially neutral with respect to pH and the ferric nitrate solution is highly acidic, the resulting aqueous ferric molybdate slurry or mixture will also be highly acidic, that is to say, it will have a pH less than about 3. Indeed, it has been found that in preparing ferric molybdate, it is critical that the pH of the mixture exists within the stated value range. Otherwise, the resultant catalyst exhibits decreased activity and selectivity toward the desired product(s). Upon mixing the two aqueous solutions, an initial light brown precipitate forms. It has been found to be critical to the performance of the catalyst that this initial brown precipitate is converted to a final bright yellow precipitate. This conversion is readily accomplished by heating the mixture at a temperature (usually 95°–100° C.) and for a time sufficient to effect such conversion (usually 1-2 hours). The bright yellow ferric molybdate precipitate is separated from the aqueous phase of the mixture and thoroughly washed to remove occluded impurities, again most notably ammonium nitrate.

As previously stated, catalyst according to this invention is that represented by the empirical formula:

$$Sb_aU_bFe_cBi_dMo_eO_f$$

where a is 1 to 10, b is 0.1 to 5, c is 0.1 to 5, d is 0.001 to 0.1, e is 0.001 to 0.2, f is a number taken to satisfy the valence requirements of Sb, U, Fe, Bi, and Mo in the oxidation states in which they exist in the catalyst. In more preferred embodiments of such catalysts, a is 1 to 5, b is 0.1 to 1, c is 0.1 to 1, d is 0.001 to 0.05, e is 0.01 to 0.1.

The catalyst preparation of this invention yields an improved catalyst that exhibits exceptional utility in the production of nitriles from olefins. Olefins suitable for use in this invention include those characterized by having at least one methyl group attached to a trigonal carbon atom. Nonlimiting representatives of such olefins include propylene, isobutylene, 2-methyl-1-pentene, 1,4-hexadiene, and the like. Of particular importance is the production of acrylonitrile from propylene and in the discussion which follows, specific reference is made to that process although it should be understood that the described catalyst is also useful for ammoxidation of other suitable olefins and for oxidation of such olefins to aldehydes and acids.

In the most frequently used ammoxidation processes, a mixture of olefin, ammonia, and oxygen (or air) is fed into a reactor and through a bed of catalyst particles at elevated temperatures. Such temperatures are usually in the range of about 400° C. to about 550° C., and preferably about 425° C. to about 500° C., and the pressure is from about 1 atmosphere to about 6 atmospheres (100 kPa to about 600 kPa). The ammonia and olefin are required stoichiometrically in equimolar amounts, but it is usually necessary to operate with a molar ratio of ammonia to olefin in excess of 1 to reduce the incidence of side reactions. Likewise, the stoichiometric oxygen requirement is 1.5 times the molar amount of olefin. The feed mixture is commonly introduced into the catalyst bed at a W/F (defined as the weight of the catalyst in grams divided by the flow of reactant stream in ml/sec. at standard temperature and pressure) in the range of about 2 g-sec/ml to about 15 g-sec/ml, preferably from about 4 g-sec/ml to about 10 g-sec/ml.

The ammoxidation reaction is exothermic and for convenience in heat distribution and removal, the catalyst bed is desirably fluidized. However, fixed catalyst beds may also be employed with alternative heat removal means such as cooling coils within the bed.

The catalyst as prepared by the process of this invention is particularly well adapted for use in such a process in that improved yields of and selectivities to the desired product(s) are experienced due to the unique and novel preparation procedures employed herein.

The following examples illustrating the best presently-known methods of practicing this invention are described in order to facilitate a clear understanding of the invention. It should be understood, however, that the expositions of the application of the invention, while indicating preferred embodiments, are given by way of illustration only and are not to be construed as limiting the invention since various changes and modifications within the spirit of the invention will become apparent to those skilled in the art from the description.

As used herein, the following terms are defined in the following manner:

1. "W/F" is defined as the weight of the catalyst in grams divided by the flow rate of the reactant stream in ml/sec. measured at STP, the units being g-sec/ml.

2. "Propylene ($C_3H_6$) conversion" is defined as:

$$\frac{\text{mols } C_3H_6 \text{ in feed} - \text{mols } C_3H_6 \text{ in effluent}}{\text{mols } C_3H_6 \text{ in feed}} \times 100$$

3. Acrylonitrile (AN) selectivity" is defined as:

$$\frac{\text{mols AN in effluent}}{\text{mols } C_3H_6 \text{ converted}} \times 100$$

4. "Acrylonitrile (AN) yield" is defined as:

$$\frac{\text{mols AN formed}}{\text{mols C}_3\text{H}_6 \text{ feed}} \times 100.$$

In the following paragraphs, the catalysts of the examples (approximately 30 g in each case), were evaluated in a fluidized bed reaction vessel having an inside diameter of about 13 mm to determine acrylonitrile selectivity and yield and propylene conversion. A reactant mixture of 17-17.8 volume percent $O_2$, 7.6-8.3 volume percent propylene ($C_3H_6$), 8-9 volume percent ammonia ($NH_3$), and the balance helium was passed upward through the catalyst bed at a rate sufficient to give the value of W/F desired. The temperature was maintained between about 425° C. and about 500° C. (preferred temperatures) and the pressure at about $200 \times 10^2$ kPa (29 psia) to about $2.50 \times 10^2$ kPa (36.3 psia) unless otherwise noted.

EXAMPLE 1

A catalyst of the composition:

$Sb_{1.86}U_{0.33}Fe_{0.67}Bi_{0.020}Mo_{0.040}O_f$-45% $SiO_2$ was prepared in the following manner.

(a) Hydrated Mixed Oxides ($Sb_{1.86}U_{0.33}Fe_{0.66}Bi_{0.020}O_f \cdot xH_2O$)—Bismuth trioxide ($Bi_2O_3$, 21.1 g, 0.045 mol) was added, with stirring, to 1830.0 g of 70% nitric acid contained in a 4-liter beaker. The solution was heated to about 60° C. and 420.6 g (0.50 mol) of triuranium octoxide ($U_3O_8$) was added over a period of 5 to 10 minutes. The generation and evolution of nitrogen oxides were observed during this period. When the generation of nitrogen oxides subsided, the solution was diluted with 600 ml of water and 1224.0 g (4.20 mols) of antimony trioxide ($Sb_2O_3$) was added to the solution. The resultant mixture was covered and heated to 100°–105° C. and maintained at this temperature for a period of time sufficient to covert the amorphous antimony trioxide to crystalline oxides of antimony, usually 2, 4, or 5-6 hours (designated in the active catalyst as A, B, and C, respectively), and thereafter cooled to ambient temperatures.

The cooled mixture was transferred to a 9-liter glass jar and a solution of 1210.5 g (3.00 mols) of ferric nitrate nonahydrate [$Fe(NO_3)_3 \cdot 9H_2O$] in 2,000 ml of water was added. The pH of the mixture was adjusted to 8 with about 3600 ml of a solution of aqueous ammonia (28%) [57% ammonium hydroxide ($NH_4OH$)] diluted with an equal volume of water. The mixture was divided into 3 equal portions and suction filtered. Each filter cake of precipitate was washed with 6 liters of water, the pH of which was adjusted to 8 by adding aqueous ammonia, to remove ammonium nitrate formed during the precipitation as well as other occluded impurities.

(b) Ferric Molybdate [$Fe_2(MoO_4)_3$]—A solution of 26.0 g (0.18 mol) of molybdenum trioxide ($MoO_3$) in 27 ml of 28% aqueous ammonia and 75 ml of water was added to a stirred solution of 48.6 g (0.12 mol) of ferric nitrate nonahydrate [$Fe(NO_3)_3 \cdot 9H_2O$] in 450 ml of water at a rate sufficient to prevent gel formation. The pH of the mixture was 2-3. The mixture was heated at 95°–100° C. until the initial light brown precipitate turned bright yellow (approximately 1-2 hours). The vessel was covered during the heating period to minimize loss of water. The aqueous phase was decanted from the precipitate, which was then reslurried in 500 ml of water, suction filtered, and washed with an additional 500 ml of water.

(c) Catalyst—To a 12-liter stainless steel container equipped with a mechanical stirrer was added 400.0 g of 40% aqueous silica sol (Nalocag 2327) and 400 ml of water. The pH was adjusted to 9 by adding a few drops of aqueous ammonia. The hydrated mixed oxide from Procedure (a) above was slurried into the silica sol in portions, alternating with additional portions of silica sol to maintain the fluidity of the slurry until a total of 4254.0 g of silica was added. The ferric molybdate from Procedure (b) above was then added to the hydrated mixed oxide-silica sol slurry (pH 9) and the pH adjusted to 9, if necessary, by the addition of aqueous ammonia. The slurry was transferred to a ball jar and ball milled for about 18 hours, or until the solid particles were reduced to a size less than 10 microns. The ball milled slurry was transferred to a stainless steel pot and concentrated until a viscosity suitable for spray-drying was obtained. At this point the volume of the slurry was approximately 7 liters. The pH was adjusted to 8, if necessary. The slurry was then spray dried at a temperature of about 150° C. The dried particles were calcined at 850° C. for 1 hour in air to produce the active catalyst supported on 45% by weight silica.

EXAMPLE 2

To demonstrate the improvement of the catalyst composition as that of the present invention, a catalyst having the same composition as that in Example 1 was prepared according to the procedure described in Example X of U.S. Pat. No. 4,018,712.

EXAMPLE 3

A catalyst of the composition:

$Sb_{2.25}Mo_{0.5}Fe_{0.5}Bi_{0.02}Mo_{0.04}$-50% $SiO_2$ was prepared in the following manner:

2.8 g. of $Bi_2O_3$ was added to 305 g. of 70% $HNO_3$ in a 2 l stirred vessel. The mixture was heated to 80° C. and 84 g. of $U_3O_8$ was added over a period of about 5 minutes. The temperature was raised to 90° C. and maintained at this temperature for 20 minutes to dissolve all the $U_3O_8$. Nitrogen oxides were generated during this period.

150 ml of water was then added and the temperature was dropped to 80° C. 196.8 g. of $Sb_2O_3$ was then added. The mixture was digested at 100° C. for 2 hours.

The mixture was cooled to room temperature and a solution of 121.2 g. of $Fe(NO_3)_3 \cdot 9H_2O$ in 1000 ml of water was added. The mixture was transferred to a 4 l beaker. Its pH was adjusted to 5 with 575 ml of solution of 1:1 mixture of $NH_4OH$ and water in 15 minutes. The mixture was allowed to stand for 1 hour and pH was further increased to 8 with 25 ml additional 1:1 $NH_4OH$ solution.

The mixture was allowed to stand overnight. It was filtered and washed 6 times with 500 ml portions of water having its pH adjusted to 8 with $NH_4OH$.

The filter cake was slurried into 836 g. of Nalco silica sol 2327 and the pH was adjusted to 9 by the addition of 1:1 $NH_4OH$ solution. An ammonium molybdate solution prepared by dissolving 3.46 g. of $MoO_3$ in a mixture of 3.6 ml of $NH_4OH$ and 10 ml of water was then added. The pH was again adjusted to 9 with $NH_4OH$ solution.

The slurry was transferred to a jar and ball milled for 18 hours. It was then concentrated to a volume of about 1800 ml. The slurry, which had a pH of 8.5, was spray dried at a temperature of 120° C. using an air pressure of 15 psig. The spray dried material was calcined at 850° C. for 1.25 hours to produce about 650 g. of catalyst.

EXAMPLE 4

The catalysts from Examples 1–3 were separately charged to reaction vessels described above and used to convert propylene to acrylonitrile (AN). The parameters and results are shown in Table 1.

TABLE 1

|  | Catalyst | | | | |
|---|---|---|---|---|---|
|  | 1-A[1] | 1-B[2] | 1-C[3] | 2[4] | 3 |
| Reaction Temp., °C. | 460 | 455 | 455 | 450 | 463 |
| Pressure, $\times 10^2$ kPa | 2.19 | 2.25 | 2.25 | 2.15 | 1.92 |
| Feed, Volume % | | | | | |
| $C_3H_6$ | 8.0 | 8.0 | 8.0 | 8.5 | 8.0 |
| $NH_3$ | 8.4 | 8.4 | 8.4 | 8.5 | 8.5 |
| $O_2$ | 17.5 | 17.5 | 17.5 | 17.4 | 17.5 |
| He | 66.1 | 66.1 | 66.1 | 65.6 | 66.1 |
| W/F, g-sec/ml | 5.0 | 4.5 | 4.5 | 5.0 | 4 |
| $C_3H_6$ Conv., % | 97.1 | 96.9 | 96.7 | 96.6 | 96.0 |
| AN | | | | | |
| Selec. % | 76.8 | 78.1 | 77.7 | 76.5 | 81.0 |
| Yield, % | 74.6 | 75.7 | 75.1 | 73.9 | 77.8 |

[1]$Sb_2O_3$ in the hydrated mixed oxides was heated 2 hours in nitric acid.
[2]$Sb_2O_3$ in the hydrated mixed oxides was heated 4 hours in nitric acid.
[3]$Sb_2O_3$ in the hydrated mixed oxides was heated 5.5 hours in nitric acid.
[4]Catalyst prepared according to the procedure described in Example X of U.S. Pat. No. 4,018,712, except that the catalyst was supported on 45% silica.

As can be seen, each of the catalysts prepared according to the improved procedure of the present invention gave higher propylene conversion and acrylonitrile selectively and yield, thereby demonstrating the improvement exhibited by the catalysts of the present invention.

Thus, it is apparent that there has been provided in accordance with the present invention, a catalyst and a process for using same that fully satisfy the objects and advantages set forth hereinabove. While the invention has been described with respecct to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A method of preparing a catalyst containing antimony, uranium, iron, bismuth, and molybdenum in a catalytically active oxidized state useful for the oxidation and ammoxidation of olefins represented by the empirical formula:

$$Sb_a U_b Fe_c Bi_d Mo_e O_f$$

where a is 1 to 10, b is 0.1 to 5, c is 0.1 to 5, d is 0.001 to 0.1, e is 0.001 to 0.2, f is a number taken to satisfy the valence requirements of Sb, U, Fe, Bi, and Mo in the oxidation states in which they exist in the catalyst, comprising (a) preparing a hydrated mixed oxides component containing antimony, uranium, iron, and bismuth by the steps of
  (i) forming a mixture of oxides or nitrates of bismuth and uranium and an oxide of antimony in nitric acid,
  (ii) heating the mixed oxides mixture at a temperature and for a time sufficient to induce formation of crystalline oxides of antimony,
  (iii) adding an aqueous solution of ferric nitrate to the mixed oxides mixture,
  (iv) adjusting the pH of the mixed oxides mixture to about 8, thereby forming a hydrated mixed oxide precipitate in an aqueous phase,
  (v) separating the hydrated mixed oxides from the aqueous phase;
(b) forming an aqueous slurry of the hydrated mixed oxides component;
(c) adjusting the pH of the hydrated mixed oxides component slurry to about 9;
(d) adding a molybdate to the hydrated mixed oxides component slurry;
(e) adjusting the pH of the hydrated mixed oxides component—molybdate component slurry to about 8–9;
(f) forming the hydrated mixed oxides component—molybdate component slurry into dry particles; and
(g) calcining the dry particles to form the active catalyst.

2. The method of claim 1 wherein the a is 1 to 5, b is 0.1 to 1, c is 0.1 to 1, d is 0.01 to 0.05, and e is 0.01 to 0.1.

3. The method of claim 1 wherein the hydrated mixed oxides component is formed from bismuth trioxide, triuranium octoxide, and ferric nitrate nonahydrate.

4. The method of claim 1 wherein the mixed oxides mixture is heated at a temperature from about 90° C. to about 110° C. for a period of time from about 2 hours to about 6 hours.

5. The method of claim 1 wherein the temperature is at least 100° C.

6. The method of claim 1 wherein the molybdate is ferric molybdate.

7. The method of claim 1 wherein the molybdate is ammonium molybdate.

8. The method of claim 1 wherein the catalyst contains a support material comprising from about 10% to about 90% by weight of the total weight of the catalyst.

9. The method of claim 7 wherein the support material comprises from about 35% to about 65% by weight of the total weight of the catalyst.

10. The method of claim 8 wherein the support material is silica.

11. The method of claim 7 wherein the support material is added during the formation of the aqueous slurry of the hydrated mixed oxides component.

12. The method of claim 1 wherein the dry particles are formed by spray-drying an aqueous slurry.

13. The method of claim 1 wherein the dry particles are calcined at a temperature from about 500° C. to about 1150° C.

14. The method of claim 12 wherein the calcination temperature is about 850° C.

* * * * *